United States Patent [19]

Umio et al.

[11] Patent Number: 4,636,520

[45] Date of Patent: Jan. 13, 1987

[54] ANTIFUNGAL COMPOSITION EMPLOYING PYRROLNITRIN IN COMBINATION WITH AN IMIDAZOLE COMPOUND

[75] Inventors: Suminori Umio, Kawanishi; Toshiaki Kamimura, Ibaraki; Takuzo Kamishita, Takatsuki; Yasuhiro Mine, Osaka, all of Japan

[73] Assignees: Fujisawa Pharmaceutical Co., Ltd.; Toko Yakuhin Kogyo Co., Ltd., both of Osaka, Japan

[21] Appl. No.: 751,560

[22] Filed: Jul. 3, 1985

[30] Foreign Application Priority Data

Jul. 16, 1984 [GB] United Kingdom ............... 8418057
Nov. 26, 1984 [GB] United Kingdom ............... 8429832

[51] Int. Cl.$^4$ .................... A61K 31/40; A61K 31/415
[52] U.S. Cl. ................................. 514/399; 514/427
[58] Field of Search ........................... 514/399, 427

[56] References Cited

U.S. PATENT DOCUMENTS

| | | | |
|---|---|---|---|
| 3,428,648 | 2/1969 | Umio et al. | 560/35 |
| 3,839,574 | 10/1974 | Godefroi et al. | 514/399 |
| 4,118,487 | 10/1978 | Regel et al. | 514/396 |
| 4,446,145 | 5/1984 | Van Bever | 514/399 |
| 4,457,938 | 7/1984 | Von Bittera et al. | 514/396 |
| 4,569,935 | 2/1986 | Rosenberg et al. | 514/396 |

OTHER PUBLICATIONS

Chemical Abstracts, vol. 70, No. 1, 6th Jan. 1969, p. 188, No. 2120H.

R. S. Gordee et al, "Evaluation of the In Vitro and In Vivo Antifungal Activity of Pyrrolnitrin", & Antimicrob. Agents Chemother., 1967, pp. 378–387.

Chemical Abstracts, vol. 64, No. 2, 17th Jan. 1966, Col. 2624 a,b.

N. Minoru et al, "Pyrrolnitrin, a New Antifungal Antibiotic. Microbiological and Toxicological Observations", & J. Antibiot. Ser. A., 18(5), pp. 211–215.

*Primary Examiner*—Allen J. Robinson
*Attorney, Agent, or Firm*—Oblon, Fisher, Spivak, McClelland, & Maier

[57] ABSTRACT

This invention relates to an antifungal composition containing pyrrolnitrin and an antimycotic imidazole compound as active ingredients.

22 Claims, No Drawings

ANTIFUNGAL COMPOSITION EMPLOYING PYRROLNITRIN IN COMBINATION WITH AN IMIDAZOLE COMPOUND

DESCRIPTION OF THE INVENTION

The present inventors found that a combination preparation comprising pyrrolnitrin and an antimycotic imidazole compound exhibits a potent antimycotic activity at lower concentrations as compared with the cases where these ingredients are used individually.

Pyrrolnitrin is a generic name of a compound 3-(2-nitro-3-chlorophenyl)-4-chloropyrrole and is known widely as an agent having antimycotic activity.

The antimycotic imidazole compound includes, 1-[(2-chlorophenyl)diphenylmethyl]-1H-imidazole, which is known as clotrimazole, 1-[2-(2,4-dichlorophenyl)-2-[(2,4-dichlorophenyl)methoxy]ethyl]-1H-imidazole, which is known as miconazole, 1-[2-[(4-chlorophenyl)methoxy]-2-(2,4-dichlorophenyl)ethyl]-1H-imidazole, which is known as econazole, 1-[2-(2,4-dichlorophenyl)2-[(2,6-dichlorophenyl)methoxy]ethyl]-1H-imidazole, which is known as isoconazole, 1-acetyl-4-[4-[[2-(2,4-dichlorophenyl)-2-(1H-imidazol-1-ylmethyl)-1,3-dioxolan-4-yl]methoxy]phenyl]piperazine, which is known as ketoconazole, 1-[2-(2,4-dichlorophenyl)-2-(2-propenyloxy)ethyl]-1H-imidazole, which is known as enilconazole, 1-[(1,1'-biphenyl)-4-ylphenylmethyl]-1H-imidazole, which is known as bifonazole, 1-[2-[(4-chlorophenylmethyl)thio]-2-(2,4-dichlorophenyl)ethyl]-1H-imidazole, which is known as sulconazole, 1-[2-[(2-chloro-3-thienyl)methoxy]-2-(2,4-dichlorophenyl)ethyl]-1H-imidazole, which is known as tioconazole, and 1-[2-(4-chlorophenyl)-2-[2,4-dichlorophenyl)methoxyimino]ethyl]-1H-imidazole, which is known as oxyconazole.

These antimycotic imidazole compounds may be used in the form of salt, such as hydrochloride, sulfate or nitrate.

The antifungal composition according to the invention contains, as active ingredients, pyrrolnitrin and an antimycotic imidazole compound. The weight ratio between the active ingredients is preferably 1:10 to 10:1, more preferably 1:3 to 3:1, still more preferably 1:2 to 2:1, but not limited thereto and may be varied depending on the kind of the pathogenic microorganisms to be controlled.

The dosage form of the antifungal composition according to the invention is not limited to any specific form. Thus, the composition may be used in any of those dosage forms and modes of use which are similar to those of known antimycotic compositions. For instance, the composition may be used in the form of a liquid, aerosol, gel, cream, powder or ointment preparation for external use, or suppositories for vaginal application.

The content of the active ingredients, namely the mixture of pyrrolnitrin and an antimycotic imidazole compound, in these preparations is generally 0.01–50% by weight, preferably 0.01–10% by weight.

The dose of the active ingredients in the antifungal composition according to the invention may be selected depending on the dosage form, the content ratio between the active ingredients, the kind of the causative microorganisms to be therapeutically controlled, the symptons and other factors. Generally, however, the dose lies in the range of 1–500 mg/kg/day, preferably 1–50 mg/kg/day.

The antifungal composition according to the invention may contain, in addition to pyrrolnitrin and an antimycotic imidazole compound as the active ingredients, an antipruritic agent, antiinflammatory agent, analgesic or local anesthetic, such as crotamiton, diphenhydramine, diphenylpyraline hydrochloride, lidocaine, Tesit, ethyl aminobenzoate, dibucaine, methyl salicylate, menthol, camphor, Lauromacrogol, glycyrrhizic acid, azulene, or a salt thereof a bactericide, such as benzalkonium chloride, chlorohexidine, dequalinium chloride, resorcinol, phenol, Tego 51, chlorobutanol, iodine, boric acid, trimethylcetylammonium pentachlorophenate, or a salt thereof, a keratolytic, such as salicyclic acid, diethyl sebacate, urea or sulfur, an astringent or reparative agent, such as zinc chloride, allantoin, dihydroxyaluminum, a salt thereof, or the like.

The antifungal composition of this invention can, in addition, to the above active ingredients contain other bases and/or additives customary used for the preparation of pharmaceutical dosage form.

For example, as a base for liquid preparations there may be exemplified water, a lower alcohol, glycerin or the like.

Preferable example of the aerosol base is freon, and a liquid base as above.

As a base for gel preparations, there may be mentioned a dilute aqueous solution of carboxy vinyl polymer and an aqueous solution of a water soluble basic substance (e.g., sodium hydroxide).

As a base for cream preparations, there may be mentioned the abovementioned base for gel preparation, an emulsifying agent such as a nonionic surface active agent and an oily substance such as liquid paraffin or an ointment base as stated below. Preferable example of the cream base is hydrophilic ointment.

As a base for powder preparations, there may be mentioned a diluent such as calcium carbonate, calcium phosphate, sugar or the like, and/or other additives such as starch, gelatin, acacia gum, magnesium stearate, aluminum stearate, silicon or the like.

As a base of ointment preparations, there may be mentioned peanut oil, olive oil, sesame oil, palm oil, paraffin oil, lanolin, petrolatum, zinc oxide, beeswax, macrogol, stearyl alcohol, propylene glycohol, or the like.

Besides, substances cited above as examples, other bases for pharmaceutical dosage form, preservatives, and other additives that are known in the art may be suitably selected for use.

Conditions for the preparation of the pharmaceutical preparation may also be selected those described in the Pharmacopoeia of Japan (Tenth Edition) or a similar manner thereof.

The antifungal composition of this invention may be used as the therapeutic agents for eumycetes infections in the treatment of, for example, dermatophytosis, mucocutaneous candidiasis, tinea versicolor and/or erythrasma such as trichophytosis, vorticosus trichophytosis, tinea profunda, trichomycosis favosa, etc., candidias such as sublimis candidias, profunda candidias, etc., tinea nigra, sporotrichosis, chromomycosis, cryptococcosis, aspergillosis, mucormycosis, coccidioidomycosis, histoplasmosis, erythema mycoticum infantile, intertrigo erosiva candidamycetica, erosio interdigitalis candidamycetica angulus infectiosus candidamyceticus, chronic mucocutaneous candidiasis or the like.

The following test example is illustrative of the effect of the antifungal composition according to the invention.

ANTIMICROBIAL TEST 1

Pyrrolnitrin (PY) alone, clotrimazole (CL) alone, a 2:1 mixture of PY and CL, a 1:1 mixture of PY and CL and 1:2 mixture of PY and CL were tested for antimicrobial activity in various strains of microorganisms. The results obtained are shown in Table 1.

Test organisms:
- a: *Candida albicans* Yu-1200
- b: *Candida albicans* FP578
- c: *Candida albicans* FP579
- d: *Candida albicans* FP580
- e: *Candida albicans* FP581
- f: *Aspergillus oryzae* IFO 5239
- g: *Staphylococcus epidermidis* 91

Preparation of test compositions:
- Composition A: PY (10 mg) was dissolved in 1 ml of ethanol, and the solution is mixed with 9 ml of sterilized water to give a milk-white suspension.
- Composition B: CL (10 mg) was dissolved in 1 ml of N,N-dimethylformamide, and the solution was mixed with 9 ml of sterilized water to give a milk-white suspension.
- Composition C: The above Compositions A and B were mixed together in a volume ratio of 2:1 to give a suspension.
- Composition D: The above Compositions A and B were mixed together in a volume ratio of 1:1 to give a suspension.
- Composition E: The above Compositions A and B were mixed together in a volume ratio of 1:2 to give a suspension.

Test method:

Plates with varied active ingredient concentrations were prepared by admixing each of Compositions A–E prepared in the above manner with Sabouraud agar medium (for test organisms a–f) or Mueller-Hinton medium (for test organism g), followed by appropriate dilution with the medium. These plates were inoculated respectively with each of the test organisms a–g and incubated under the conditions given below, and the minimum inhibitory concentration (MIC; $\mu g/ml$) at which the growth of each test organism is inhibited was determined.

Incubation conditions

For test organisms a–e, incubation was performed, following inoculation, at 37° C. for 24 hours.

For test organism f, incubation was conducted, following inoculation, at 30° C. for 1 week.

For test organisms g, incubation was carried out, following inoculation, at 37° C. for 20 hours.

Results:

TABLE 1

| Test organisms | MIC values ($\gamma$/ml) [The figures in the parentheses indicate the FIC index values] | | | | |
|---|---|---|---|---|---|
| | Compn. A | Compn. B | Compn. C | Compn. D | Compn. E |
| a | 100 | 6.25 | 0.78 (0.047) | 1.56 (0.133) | 1.56 (0.172) |
| b | 3.13 | 6.25 | 0.39 (0.104) | ≦0.20 (≦0.05) | 0.78 (0.166) |
| c | 25.0 | 6.25 | 0.78 (0.062) | 1.56 (0.156) | 0.78 (0.260) |
| d | 1.56 | 6.25 | 0.39 (0.187) | 0.39 (0.156) | 0.39 (0.125) |
| e | >100 | 25.0 | 12.5 | 12.5 | 12.5 |
| f | >100 | 12.5 | 6.25 (0.250) (0.208) | 6.25 (0.313) (0.281) | 6.25 (0.375) (0.354) |
| g | 100 | 25.0 | 12.5 (0.50) | 12.5 (0.313) | (0.375) |

ANTIMICROBIAL TEST 2

Pyrrolnitrin (PY) alone, clotrimazole (CL) alone, miconazole alone, econazole alone, oxyconazole alone and 1:1 mixtures of PY and CL, PY and miconazole, PY and econazole and PY and oxyconazole were test for antimicrobial activity in various strains of microorganisms. The results obtained are shown in Table 2.

Test organisms:
- a: *Candida albicans* Yu-1200
- d: *Candida albicans* FP580

Preparation of test compositions:
- Compositions A was prepared as stated above.
- Composition F, G and H: A milk-white suspension containing 10 mg of miconazole (Composition F), a transparent solution containing 10 mg of econazole (Composition G) and a milk-white suspension containing 10 mg of oxyconazole (Composition H) were respectively prepared in a similar way to that of Composition B.
- Composition I: The above-mentioned Compositions A and F were mixed together in a volume ratio of 1:1 to give a suspension.
- Composition J: The above-mentioned Compositions A and G were mixed together in a volume ratio of 1:1 to give a suspension.
- Composition K: The above-mentioned Compositions A and H were mixed together in a volume ratio of 1:1 to give a suspension.

Test method:

Plates with varied active ingredient concentrations were prepared by admixing each of Compositions A and F to K prepared in the above manner with Sabouraud agar medium, followed by appropriate dilution with the medium. These plates were inoculated respectively with each of the test organisms a and d and incubated at 30° C. for 48 hours. The minimum inhibitory concentration (MIC; $\mu g/ml$) at which the growth of each test organism is inhibited was determined.

Results:

TABLE 2

| Composition | MIC values ($\gamma$/ml) [The figures in the parentheses indicate the FIC index values] | |
|---|---|---|
| | Test organisms | |
| | a | d |
| A | 100 | 0.78 |
| F | 6.25 | 12.5 |
| G | 6.25 | 6.25 |
| H | 25 | 25 |
| I | 0.39 (0.033) | 0.39 (0.266) |
| J | 0.39 (0.033) | 0.39 (0.281) |
| K | 0.78 (0.020) | 0.39 (0.258) |

The FIC indexes given in the parentheses of Tables 1 and 2 were calculated by using the following formulas.

For Composition C $$FIC = \frac{MIC \text{ of Composition } C \times 2}{MIC \text{ of Composition } A \times 3} + \frac{MIC \text{ of Composition } C}{MIC \text{ of Composition } B \times 3}$$

For Composition D $$FIC = \frac{MIC \text{ of Composition } D}{MIC \text{ of Composition } A \times 2} + \frac{MIC \text{ of Composition } D}{MIC \text{ of Composition } B \times 2}$$

For Composition E $$FIC = \frac{MIC \text{ of Composition } E}{MIC \text{ of Composition } A \times 3} + \frac{MIC \text{ of Composition } E \times 2}{MIC \text{ of Composition } B \times 3}$$

For Composition I $$FIC = \frac{MIC \text{ of Composition } I}{MIC \text{ of Composition } A \times 2} + \frac{MIC \text{ of Composition } I}{MIC \text{ of Composition } F \times 2}$$

For Composition J $$FIC = \frac{MIC \text{ of Composition } J}{MIC \text{ of Composition } A \times 2} + \frac{MIC \text{ of Composition } J}{MIC \text{ of Composition } G \times 2}$$

For Composition K $$FIC = \frac{MIC \text{ of Composition } K}{MIC \text{ of Composition } A \times 2} + \frac{MIC \text{ of Composition } K}{MIC \text{ of Composition } H \times 2}$$

It is generally recognized that when the FIC index is below 1.0, there is a synergism. The FIC index for each of the antifungal compositions according to the invention containing PY and an antimycotic imidazole compound is less than 1 for almost all of the test organisms. It is thus evident that the combination of PY with an antimycotic imidazole compound produces a strong synergism, and accordingly the composition of this invention is useful as an antifungal agent. In particular, it is useful as a therapeutic agent for mycosis, especially candidiasis.

The following examples are preferred embodiments of the compositions according to the invention. It is to be noted, however, that these examples are by no means limitative of the invention and that various pharmaceutical modifications, for instance addition of a third active ingredient and improvement in the manufacturing process, are all fall under the scope of this invention.

EXAMPLE 1

| | |
|---|---|
| Pyrrolnitrin | 2.5 g |
| Clotrimazole | 5.0 g |
| Olive oil | 100.0 g |
| Pure lanolin | 80.0 g |
| White petrolatum | 812.5 g |

Pyrrolnitrin (2.5 g) and 5.0 g of clotrimazole are dissolved in a mixture of 100.0 g of olive oil, 80.0 g of pure lanolin and 812.5 g of white petrolatum with warming, followed by stirring for homogenization. An oleaginous ointment is thus produced.

EXAMPLE 2

| | |
|---|---|
| Pyrrolnitrin | 5.0 g |
| Clotrimazole | 2.5 g |
| Zinc oxide | 200.0 g |
| Pure lanolin | 105.0 g |
| Bleached beeswax | 40.0 g |
| White petrolatum | 647.5 g |

Zinc oxide (200.0 g) and 105.0 g of pure lanolin are triturated until the mixture becomes homogeneous. Separately, 5.0 g of pyrrolnitrin and 2.5 g of clotrimazole are dissolved in a mixture of 40.0 g of bleached beeswax and 647.5 g of white petrolatum with warming, followed by stirring for homogenization. To this solution is added the above zinc oxide-pure lanolin triturate, followed by stirring until the whole mixture becomes homogeneous. An oleaginous ointment is thus produced.

EXAMPLE 3

| | |
|---|---|
| Pyrrolnitrin | 2.5 g |
| Clotrimazole | 5.0 g |
| Macrogol 4000 | 496.25 g |
| Macrogol 400 | 496.25 g |

Pyrrolnitrin (2.5 g) and 5.0 g of clotrimazole are dissolved in a mixture of 496.25 g of Macrogol 4000 and 496.25 g of Macrogol 400 with warming, followed by stirring for homogenization. A hydrophilic ointment is thus produced.

EXAMPLE 4

| | |
|---|---|
| Pyrrolnitrin | 2.50 g |
| Clotrimazole | 5.00 g |
| White petrolatum | 250.00 g |
| Stearyl alcohol | 220.00 g |
| Propylene glycol | 120.00 g |
| Sodium lauryl sulfate | 15.00 g |
| Methylparaben | 0.25 g |
| Propylparaben | 0.15 g |
| Purified water | 387.10 g |

Pyrrolnitrin (2.5 g) and 5.00 g of clotrimazole are dissolved in a mixture of 250.00 g of white petrolatum, 220.00 g of stearyl alcohol, 120.00 g of propylene glycol and 0.15 g of propylparaben with warming, followed by stirring for homogenization.

Separately, 15.00 g of sodium lauryl sulfate and 0.25 g of methylparaben are dissolved in 387.10 g of purified water with warming, followed by stirring for homogenization. Thereafter, the above active ingredient solution is added, and the whole mixture is stirred until emulsification and homogenization are complete. An emulsion ointment is thus obtained.

EXAMPLE 5

| Pyrrolnitrin | 2.5 g |
|---|---|
| Clotrimazole | 5.0 g |
| White petrolatum | 400.0 g |
| Cetyl alcohol | 180.0 g |
| Sorbitan sesquioleate | 50.0 g |
| Lauromacrogol | 5.0 g |
| Methylparaben | 1.0 g |
| Propylparaben | 1.0 g |
| Purified water | 355.5 g |

Pyrrolnitrin (2.5 g) and 5.0 g of clotrimazole are dissolved in a mixture of 400.0 g of white petrolatum, 180.0 g of cetyl alcohol, 50.0 g of sorbitan sesquioleate and 1.0 g of propylparaben with warming, followed by stirring for homogenization. Separately, 5.0 g of Lauromacrogol and 1.0 g of methylparaben are dissolved in purified water with warming, followed by stirring for homogenization. Thereafter, the above-obtained active ingredient solution is added, followed by stirring until emulsification and homogenization are complete. An emulsion ointment is thus produced.

EXAMPLE 6

| Pyrrolnitrin | 2.5 g |
|---|---|
| Clotrimazole | 5.0 g |
| Polyethylene glycol (10 E.O.) monolaurate | 100.0 g |
| Propylene glycol | 60.0 g |
| Diisopropyl adipate | 20.0 g |
| Ethanol | 400.0 g |
| Carboxyvinyl polymer | 12.0 g |
| Diisopropanolamine | 1.5 g |
| Purified water | 399.0 g |

Pyrrolnitrin (2.5 g) and 5.0 g of clotrimazole are dissolved in a mixture of 100.0 g of polyethylene glycol (10 E.O.) monolaurate, 60.0 g of propylene glycol, 20.0 g of diisopropyl adipate and 400.0 g of ethanol, and 240 g of 5% aqueous solution of carboxyvinyl polymer is added, followed by stirring. To the mixture is added a solution of 1.5 g of diisopropanolamine in 150 g of purified water, followed by addition of purified water to make 1000 g. Stirring is continued until the whole mixture becomes homogeneous. A gel preparation for external use is thus produced.

EXAMPLE 7

| Pyrrolnitrin | 2.5 g |
|---|---|
| Clotrimazole | 5.0 g |
| Stearyl alcohol | 250.0 g |
| Stearic acid | 50.0 g |
| Macrogol 6000 | 50.0 g |
| Hexanetriol | 50.0 g |
| Propylene glycol | 400.0 g |
| Macrogol 400 | 192.5 g |

Pyrrolnitrin (2.5 g) and 5.0 g of clotrimazole are dissolved in 400.0 g of propylene glycol with warming, followed by stirring for homogenization. Separately, 250.0 g of stearyl alcohol, 50.0 g of stearic acid, 50.0 g of Macrogol 6000, 50.0 g of hexanetriol and 192.5 g of Macrogol 400 are dissolved with warming, followed by stirring for homogenization. Thereafter, the above active ingredient solution is added, followed by stirring until the whole mixture becomes homogeneous. A gel preparation for external use is thus produced.

EXAMPLE 8

| Pyrrolnitrin | 2.5 g |
|---|---|
| Clotrimazole | 5.0 g |
| Glycerin | 30.0 g |
| Ethanol | 700 ml |
| Purified water | q.s. |

Pyrrolnitrin (2.5 g) and 5.0 g of clotrimazole are dissolved in a mixture of 30.0 g of glycerin and 700 ml of ethanol, followed by addition of purified water to make 1000 ml and stirring until the mixture becomes homogeneous. A tincture for external use is thus produced.

EXAMPLE 9

| Pyrrolnitrin | 5.0 g |
|---|---|
| Clotrimazole | 2.5 g |
| Zinc oxide, finely divided | 100.0 g |
| Starch | 142.5 g |
| Talc | 750.0 g |

The above components are each passed through a No. 100 sieve and homogeneously mixed together. A powder for external use is produced.

EXAMPLE 10

| Pyrrolnitrin | 2.5 g |
|---|---|
| Clotrimazole | 5.0 g |
| Ethanol | 352.5 g |
| Freon (1:1 mixture of Freon-11 and Freon-12) | 64.0 g |

Pyrrolnitrin (2.5 g) and 5.0 g of clotrimazole are dissolved in 352.5 g of ethanol, and 64.0 g of Freon is added. The mixture is then packed in an aerosol container. An aerosol is thus produced.

EXAMPLE 11

| Pyrrolnitrin | 2.5 g |
|---|---|
| Clotrimazole | 5.0 g |
| Wax | 15.0 g |
| Ethanol | 547.5 g |
| Polyvinylpyrrolidone | 20.0 g |
| Deionized water | 330.0 g |
| Freon (1:1 mixture of Freon-11 and Freon-12) | 8.0 g |

Pyrrolnitrin (2.5 g) and 5.0 g of clotrimazole are dissolved in 547.5 of ethanol, and 15.0 g of wax, 20.0 g of polyvinylpyrrolidone and 330.0 g of deionized water are added, followed by stirring for homogenization. To the solution is added 8.0 g of Freon and the mixture is packed in an aerosol container. An aerosol is thus produced.

EXAMPLE 12

| Pyrrolnitrin | 5.0 g |
|---|---|
| Clotrimazole | 2.5 g |
| Olive oil | 100.0 g |
| Pure lanolin | 80.0 g |
| White petrolatum | 812.5 g |

The above components are treated in the same manner as Example 1 to give an oleaginous ointment.

EXAMPLE 13

| | |
|---|---|
| Pyrrolnitrin | 5.0 g |
| Clotrimazole | 2.5 g |
| Glycerin | 30.0 g |
| Ethanol | 700 ml |
| Purified water | q.s. |

The above components are treated in the same manner as Example 8 to give a tincture for external use.

EXAMPLE 14

| | |
|---|---|
| Pyrrolnitrin | 3.75 g |
| Clotrimazole | 3.75 g |
| Zinc oxide | 200.0 g |
| Pure lanolin | 105.0 g |
| Bleached beeswax | 40.0 g |
| White petrolatum | 647.5 g |

The above components are treated in the same manner as Example 2 to give an oleaginous ointment.

EXAMPLE 15

| | |
|---|---|
| Pyrrolnitrin | 2.5 g |
| Clotrimazole | 5.0 g |
| Crotamiton | 20.0 g |
| Ethyl alcohol | 400.0 g |
| 4% Aqueous solution of carboxyvinyl polymer | 400.0 g |
| 20% Aqueous solution of monoethanolamine | 80.0 g |
| Purified water | 92.5 g |

Pyrrolnitrin and clotrimazole are dissolved in crotamiton at about 70°–80° C., followed by addition of ethyl alcohol to make a homogeneous solution. 4% Aqueous solution of carboxyvinyl polymer and then 20% aqueous solution of monoethanolamine are added portionwise to the solution with stirring. To this solution is added purified water to make 1000 g, and the solution is thoroughly stirred and then cooled. A transparent gel preparation is thus produced.

EXAMPLE 16

| | |
|---|---|
| Pyrrolnitrin | 2.5 g |
| Clotrimazole | 5.0 g |
| Crotamiton | 20.0 g |
| Isopropyl myristate | 100.0 g |
| Propylene glycol | 100.0 g |
| Polyoxyethylene sorbitan monolaurate | 10.0 g |
| 4% Aqueous solution of carboxyvinyl polymer | 170.0 g |
| 1% Aqueous solution of disodium edetate | 12.0 g |
| 2% Aqueous solution of sodium hydroxide | 20.0 g |
| Purified water | 560.5 g |

Pyrrolnitrin and clotrimazole are dissolved in crotamiton at about 70° C., and isopropyl myristate, propylene glycol, Polyoxyethylene sorbitan monolaurate, 4% aqueous solution of carboxyvinyl polymer, 530 g of purified water and 1% aqueous solution of disodium edetate are serially added to the solution. With stirring at about 70°–80° C., 2% aqueous solution of sodium hydroxide is added to the above solution, followed by addition of purified water to make 1000 g and cooling. A cream for external use is thus produced.

EXAMPLE 17

| | |
|---|---|
| Pyrrolnitrin | 3.75 g |
| Oxyconazole | 3.75 g |
| Olive oil | 100.0 g |
| Pure lanolin | 80.0 g |
| White petrolatum | 812.5 g |

Pyrrolnitrin and oxyconazole are dissolved in a mixture of olive oil, pure lanolin and white petrolatum with warming, followed by stirring for homogenization. An oleaginous ointment is thus prepared.

EXAMPLE 18

| | |
|---|---|
| Pyrrolnitrin | 2.0 g |
| Econazole | 4.0 g |
| Glycerin | 30.0 g |
| Ethanol | 700 ml |
| Purified water | q.s. |

Pyrrolnitrin and econazole are dissolved in a mixture of glycerin and ethanol, followed by addition of purified water to make 1000 ml and stirring until the mixture becomes homogeneous. A tincture for external use is thus produced.

EXAMPLE 19

| | |
|---|---|
| Pyrrolinitrin | 5.0 g |
| Miconazole | 2.5 g |
| Crotamiton | 20.0 g |
| Isopropyl myristate | 100.0 g |
| Propylene glycol | 100.0 g |
| Polyoxyethylene sorbitan monolaurate | 10.0 g |
| 4% Aqueous solution of carboxyvinyl polymer | 170.0 g |
| 1% Aqueous solution of disodium edetate | 12.0 g |
| 2% Aqueous solution of sodium hydroxide | 20.0 g |
| Purified water | 560.5 g |

Pyrrolnitrin and miconazole are dissolved in crotamiton at about 70° C., and isopropyl myristate, propylene glycol, Polyoxyethylene sorbitan monolaurate, 4% aqueous solution of carboxyvinyl polymer, 530 g of purified water and 1% aqueous solution of disodium edetate were serially added to the solution. With stirring at about 70°–80° C., 2% aqueous solution of sodium hydroxide is added to the above solution, followed by addition of purified water to make 1000 g and cooling. A cream for external use is thus produced.

EXAMPLE 20

| | |
|---|---|
| Pyrrolnitrin | 2.0 g |
| Miconazole | 4.0 g |
| Glycerin | 30.0 g |
| Ethanol | 700 ml |
| Purified water | q.s. |

Pyrrolnitrin and miconazole are dissolved in a mixture of glycerin and ethanol, followed by addition of purified water to make 1000 ml and stirring until the mixture becomes homogeneous. A tincture for external use is produced.

What is claimed is:

1. An antifungal composition which contains, as active ingredients 1 part of 3-(2-nitro-3-chlorophenyl)-4-chloropyrrole and 1 part of an antimycotic imidazole compound selected from the group consisting of clotrimazole, miconazole, econazole and oxyconazole.

2. The antifungal composition according to claim 1, wherein the antimycotic imidazole compound is clotrimazole.

3. The antifungal composition according to claim 1, wherein the antimycotic imidazole compound is miconazole.

4. The antifungal composition according to claim 1, wherein the antimycotic imidazole compound is econazole.

5. The antifungal composition according to claim 1, wherein the antimycotic imidazole compound is oxyconazole.

6. An antifungal composition which contains admixed in an inert carrier, an antifungally effective amount of, as active ingredients, 1 part of 3-(2-nitro-3-chlorophenyl)-4-chloropyrrole and 1 part of an antimycotic imidazole compound selected from the group consisting of clotrimazole, miconazole, econazole, and oxyconazole.

7. The antifungal composition according to claim 6, wherein the antimycotic imidazole compound is clotrimazole.

8. The antifungal composition according to claim 6, wherein the antimycotic imidazole compound is miconazole.

9. The antifungal composition according to claim 6, wherein the antimycotic imidazole compound is econazole.

10. The antifungal composition according to claim 6, wherein the antimycotic imidazole compound is oxyconazole.

11. The antifungal composition according to claim 6, wherein the antifungally effective amount is 0.01-10% by weight.

12. The antifungal composition according to claim 11, wherein the antimycotic imidazole compound is clotrimazole.

13. The antifungal composition according to claim 11, wherein the antimycotic imidazole compound is miconazole.

14. The antifungal composition according to claim 11, wherein the antimycotic imidazole compound is econazole.

15. The antifungal composition according to claim 11, wherein the antimycotic imidazole compound is oxyconazole.

16. A method for treatment of fungus in a subject in need of treatment which comprises administering to the subject an antifungally effective amount of the composition of claim 1.

17. The method of claim 16 wherein the antifungally effective amount is 1-500 mg/kg/day.

18. An antifungal composition which contains, as active ingredients, 1 to 3 parts of 3-(2-nitro-3-chlorophenyl)-4-chloropyrrole and 3 to 1 parts of clotrimazole.

19. An antifungal composition which contains, admixed in an inert carrier, an antifungally effective amount of, as active ingredients, 1 to 3 parts of 3-(2-nitro-3-chlorophenyl)-4-chloropyrrole and 3 to 1 parts of clotrimazole.

20. The antifungal composition according to claim 19, wherein the antifungally effective amount is 0.01-10% by weight.

21. A method for treatment of fungus in a subject in need of treatment which comprises administering to the subject an antifungally effective amount of the composition of claim 18.

22. The method of claim 21, wherein the antifungally effective amount is 1-500 mg/kg/day.

* * * * *